United States Patent [19]
Dunn et al.

[11] Patent Number: 5,945,115
[45] Date of Patent: *Aug. 31, 1999

[54] POLYMERIC COMPOSITIONS USEFUL AS CONTROLLED RELEASE IMPLANTS

[75] Inventors: Richard L. Dunn; Arthur J. Tipton, both of Fort Collins, Colo.

[73] Assignee: Atrix Laboratories, Inc., Fort Collins, Colo.

[ * ] Notice: This patent is subject to a terminal disclaimer.

[21] Appl. No.: 08/908,263

[22] Filed: Aug. 8, 1997

Related U.S. Application Data

[63] Continuation of application No. 08/070,498, Jun. 2, 1993, Pat. No. 5,702,216, which is a continuation of application No. 07/776,816, Oct. 15, 1991, abandoned.

[51] Int. Cl.$^6$ ...................................................... A61K 9/20
[52] U.S. Cl. ........................ 424/422; 424/423; 424/424; 424/426; 424/427; 424/430; 424/434; 424/437; 523/105; 523/113
[58] Field of Search ..................................... 424/422, 423, 424/424, 426, 427, 430, 434, 437; 523/105, 113

[56] References Cited

U.S. PATENT DOCUMENTS

| | | | |
|---|---|---|---|
| 2,155,658 | 4/1939 | Herrmann | 514/772.2 |
| 3,068,188 | 12/1962 | Beste | 524/173 |
| 3,219,527 | 11/1965 | Gurney | 424/435 |
| 3,328,246 | 6/1967 | Gottfried | 424/435 |
| 3,458,622 | 7/1969 | Hill | 424/19 |
| 3,767,784 | 10/1973 | Gluck | 128/156 |
| 3,887,699 | 6/1975 | Yolles | 424/477 |
| 3,931,678 | 1/1976 | O'Sullivan | 433/228.1 |
| 4,088,798 | 5/1978 | Michaelis | 427/3 |
| 4,127,127 | 11/1978 | Wong | 424/424 |
| 4,161,948 | 7/1979 | Bichon | 128/156 |
| 4,447,562 | 5/1984 | Ivani | 523/105 |
| 4,450,150 | 5/1984 | Sidman | 424/426 |
| 4,491,479 | 1/1985 | Lauchenauer | 128/156 |
| 4,568,536 | 2/1986 | Kronenthal | 514/900 |
| 4,570,629 | 2/1986 | Widra | 128/156 |
| 4,582,640 | 4/1986 | Smestad | 128/DIG. 8 |
| 4,614,787 | 9/1986 | Szycher | 528/75 |
| 4,631,188 | 12/1986 | Stoy | 424/81 |
| 4,650,665 | 3/1987 | Kronenthal | 424/435 |
| 4,677,139 | 6/1987 | Feinmann | 128/90 |
| 4,715,369 | 12/1987 | Suzuki | 424/435 |
| 4,745,160 | 5/1988 | Churchill | 523/105 |
| 4,767,627 | 8/1988 | Caldwell | 424/426 |
| 4,772,470 | 9/1988 | Inoue | 424/435 |
| 4,774,227 | 9/1988 | Piez | 128/DIG. 8 |
| 4,920,203 | 4/1990 | Tang | 523/105 |
| 4,933,182 | 6/1990 | Higashi | 424/435 |
| 4,938,763 | 7/1990 | Dunn | 604/891.1 |
| 4,946,870 | 8/1990 | Partain, III | 514/777 |
| 5,077,049 | 12/1991 | Dunn | 424/426 |

FOREIGN PATENT DOCUMENTS

| | | |
|---|---|---|
| 0140766 | 5/1985 | European Pat. Off. . |
| 0430474 | 6/1991 | European Pat. Off. . |
| 29 17 037 | 4/1980 | Germany . |
| 226514 | 2/1990 | New Zealand . |

OTHER PUBLICATIONS

Juni et al., *Chem. Pharm. Bull.* 33:1609–1614 (1985).

*Primary Examiner*—Raj Bawa
*Attorney, Agent, or Firm*—Merchant & Gould P.C.

[57] ABSTRACT

The invention is directed to an improved system for controlled release of biologically active materials and to a liquid composition for its formation. The liquid composition is composed of a thermoplastic polymer, rate modifying agent, bioactive material and organic solvent. The liquid composition is capable of forming a biodegradable and/or bioerodible microporous, solid polymer matrix. The matrix is useful as an implant in patients (humans and animals) for delivery of biologically active substances to tissues or organs.

4 Claims, No Drawings

POLYMERIC COMPOSITIONS USEFUL AS CONTROLLED RELEASE IMPLANTS

This application is a Continuation of application Ser. No. 08/070,498, now U.S. Pat. No. 5,702,216, filed Jun. 2, 1993, now U.S. Pat. No. 5,702,716 which is a continuation of application Ser. No. 07/776,816, filed Oct. 15, 1991, now abandoned, which is incorporated by reference.

BACKGROUND OF THE INVENTION

Biodegradable polymers are useful in many medical applications, especially drug delivery devices. Many of the biodegradable polymers used are of the thermoplastic type. Polymers made of thermoplastic resins typically liquify or soften at elevated temperatures and resolidify upon cooling. This type of polymer is generally formed into the desired structure for use as sutures, surgical clips, staples, implants, and the like, prior to insertion into the body. Once inserted into the body, these polymers retain their shape.

For drug delivery devices, the drug is generally incorporated into the polymeric composition and formed into the desired shape outside the body. This solid implant is then typically inserted into the body of a human, animal, bird, and the like through an incision. Alternatively, small discrete particles composed of these polymers can be injected into the body by a syringe. Preferably, however, certain of these polymers can be injected via syringe as a liquid polymeric composition.

Liquid polymeric compositions for use as biodegradable controlled release drug delivery systems are described in U.S. Pat. No. 4,938,763, issued to Dunn et al. These compositions are administered to the body in a liquid state or, alternatively, as a solution, typically via syringe. Once in the body the composition coagulates or cures into a solid. One type of polymeric composition consists of a nonreactive thermoplastic polymer or copolymer dissolved in a water-miscible solvent. This polymeric solution is placed into the body where the polymer congeals or precipitatively solidifies upon the dissipation or diffusion of the solvent into the surrounding body tissues.

The presence of a plasticizer within a sustained release composition is known to advance or speed up the release of bioactive material by the sustained release polymer. Known plasticizers have been used to enhance the delivery of drugs from diffusional therapeutic systems. For example, K. Juni et al., *Chem. Pharm. Bull.,* 33, 1609 (1985) disclose that the release rate of bleomycin from polylactic acid microspheres is greatly enhanced by incorporating fatty acid esters into the microspheres. U.S. Pat. No. 4,127,127, issued to Wong et al., discloses systems made from films of segmented copolyesters of butylene terephthalate and polyalkylene ether terephthalate that incorporate plasticizers to create a more diffusible system. Water-insoluble liquid plasticizers are used to "soften" the copolyester and cause its diffusion coefficient to increase, thereby enhancing the diffusion of nonionic drugs. Water-soluble plasticizers are used to create a water-swollen microporous structure, by leaching slowly from the copolyester, to make the composition more permeable to drugs.

Although the liquid polymeric systems as described by Dunn et al. have proven to be beneficial in many respects, they do not enable variable control of release rate, especially control such that the rate is slower. Consequently, there is the need for a liquid composition in which the rate of drug delivery can be more readily controlled especially for a drug that requires longer term release.

It is, therefore, an object of the present invention to provide an improved composition comprising a biodegradable or bioerodible polymer for use as an implant in the body of a human, bird, fish, etc. Another object is to provide an improved polymeric composition for a diffusional therapeutic delivery system that can be administered to an implant site in liquid form. Yet another object is to provide an improved polymeric composition that forms a solid matrix in situ thereby forming an implant for sustained release of a medicament over a desired period of time. A further object is to provide a liquid or solution polymeric composition that can form in situ a biodegradable solid or gelatinous drug delivery system wherein the amount and rate of the material delivered can be controlled, more precisely, especially when long-term release is required.

SUMMARY OF THE INVENTION

The present invention is directed to a polymer system, a method for therapeutic treatment using the polymer system, and a precursor of the polymer system, a liquid composition.

The polymer system is a microporous, solid matrix of a biocompatible, biodegradable thermoplastic polymer, a rate modifying agent and a bioactive material. The system displays control of the rate and extent of release of the bioactive agent from the matrix. As used herein, the term "biologically active material" or "bioactive material" means a drug, medicament, or some other substance capable of producing an effect on a body, e.g., a mammal.

The liquid composition is a combination of an organic solvent, the biocompatible, biodegradable thermoplastic polymer, the rate modifying agent and the bioactive material.

The polymer system is formed by applying the liquid composition to an aqueous medium that is internal (body fluids) or external to the body. After application, the liquid composition coagulates to form the polymer system. Administration of the liquid composition directly into the body forms in situ the polymer system. External addition of the liquid composition to an aqueous liquid forms the polymer system outside the body. The solid implantable polymer system can then be surgically placed into the body. In all embodiments and applications, the polymer system is substantially insoluble in aqueous media.

The process by which the polymer system is formed in part is responsible for development of the rate and release control. Interaction of the liquid composition with an aqueous medium either in situ in the body or external to the body to coagulate the composition into the polymer system at least in part causes the desired controlled release profile as a function of the variation of the below-mentioned parameters and components. Simple combination of these components without passage through the liquid composition will not develop the controlled release profile of this invention.

When the liquid composition is added to the aqueous medium, the organic solvent diffuses into the surrounding medium (body fluids or an external water medium) and the polymer coagulates to form the solid matrix (polymer system). The more or less simultaneous diffusion and coagulation produce the microporous structure of the matrix that in part is believed to be a factor in the establishment of the desired control of rate and extent of release. Under certain conditions of the invention, the structure exhibits a core with large pores of diameters from about 10 to 500 microns and a relatively nonporous skin. The skin in this preferred embodiment actually has extremely fine pores of 0.01 to 0.1 microns in diameter.

Although it is not important for some uses, when the composition is placed in the body, the resulting polymer system adopts the shape of the cavity, pocket or intercellular space into which the composition is placed. When the polymer system is formed outside the body it can be molded or adapted into substantially the appropriate shape of the cavity or other space of the body into which it is being fitted.

Pursuant to the parameters and conditions of the invention, the polymer system can control the sustained release of biologically active materials in vivo. In particular, the rate and extent of release of the biologically active material from the polymer system of the invention are controlled over a range of speeds and amounts. This control is accomplished by variation of: (a) the polymer type and molecular weight, (b) the rate modifying agent, (c) the concentration of the polymer, (d) concentration of the biologically active material, (e) the form of the biologically active material, and (f) the concentration and kinds of other additives present, if any, within the polymer system. Preferably, the rate and extent of release of bioactive material from the polymer system according to the invention can be controlled by varying: (1) the type and molecular weight of the polymer or polymers, (2) the concentration of a suitable rate modifying agent, or a mixture of rate modifying agents and/or (3) the concentration of the polymer. More preferably, the control is accomplished by varying the molecular weight of the polymer and/or the concentration of the rate modifying agent present. Most preferably, the control is accomplished by varying both the molecular weight of the polymer and the concentration of the rate modifying agent. In preferred embodiments, the rate of release increases as polymer molecular weight increases, and independent of the polymer molecular weight, the rate of release increases as the concentration of the plasticizer decreases.

The method of the invention is based upon the therapeutic effect of the in situ controlled release of the bioactive material from the polymer system. The implantation of the liquid composition or implantation of the polymer system preformed as described above can generally occur anywhere within the body of a patient in need of therapeutic treatment. Examples include soft tissue such as muscle or fat; hard tissue such as bone; or a cavity or pocket such as the periodontal, oral, vaginal, rectal, nasal, or the cul-de-sac of the eye. The composition can be administered to the implant site by any suitable method for applying a liquid, as for example, by means of a syringe, needle, cannula or catheter. The polymer system preformed as an implant can be inserted by known surgical techniques.

DETAILED DESCRIPTION OF THE INVENTION

The present invention relates to a polymer system for the controlled delivery of bioactive materials, a liquid composition for producing such a system, and a method for use of such a system in therapeutic treatment. The polymer system of the present invention is advantageous in that it can be manipulated to control the amount of bioactive material released and the rate at which it is released in vivo.

The polymer system is prepared by combining the liquid composition and an aqueous medium to coagulate the composition into a solid, microporous polymeric matrix. The liquid composition contains a thermoplastic polymer or copolymer in combination with a suitable solvent and rate modifying agent. The polymers or copolymers, which form the body of the matrix, are substantially insoluble, preferably essentially completely insoluble, in water and body fluids. The insolubility of the matrix body enables it to function as a single site for the controlled release of bioactive material. The polymers or copolymers also are biocompatible and biodegradable and/or bioerodible within the body of an animal, e.g., mammal. The biodegradation enables the patient to metabolize the polymer matrix so that it can be excreted by the patient without the need for further surgery to remove it. Because the liquid composition and polymer system are biocompatible, the insertion process and the presence of the polymer system within the body do not cause substantial tissue irritation or necrosis at the implant site.

The liquid composition can be administered as a liquid directly into body tissues or cavities wherein an implant of the polymer system is formed in situ. Alternatively, the liquid composition can be externally combined with an aqueous medium to form an implantable polymer system. The implantable polymer system is then inserted surgically into the body.

Thermoplastic Polymer

Suitable thermoplastic polymers for incorporation as the solid matrix of the controlled release polymer system are solids, pharmaceutically compatible and biodegradable by cellular action and/or by the action of body fluids. Examples of appropriate thermoplastic polymers include polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid) polymers, polymaleic anhydrides, poly(methylvinyl) ethers, poly(amino acids), chitin, chitosan, and copolymers, terpolymers, or combinations or mixtures of the above materials.

Preferred materials are the polylactides, polyglycolides, polycaprolactones, and copolymers thereof. These polymers can be used to advantage in the polymer system in part because they show excellent biocompatibility. They produce little, if any, tissue irritation, inflammation, necrosis, or toxicity. In the presence of water, these polymers produce lactic, glycolic, and hydroxycaproic acid, respectively, which are readily metabolized by the body. The polylactides and polycaprolactones can also incorporate glycolide monomer to enhance the resulting polymer's degradation.

Depending on the desired softness and flexibility of the implant rate and extent of bioactive material release, rate of degradation, and the like, the amount and type of polymer can be varied to produce the desired result. For example, for a relatively soft and flexible polymer system, copolymers with a low Tg can be used, primarily the lactide/caprolactone copolymers. The ratio of glycolide to lactide or to caprolactone can also be varied to effect water diffusibility, which increases with an increasing amount of the more hydrophilic monomer. The hydrophilic character of these monomers increases in the series as caprolactone<lactide<glycolide.

The solubility or miscibility of a thermoplastic polymer in the organic solvent of the composition will vary according to factors such as crystallinity, hydrophilicity, capacity for hydrogen bonding and molecular weight of the polymer. Consequently, the molecular weight and the concentration of the polymer in the solvent are adjusted to achieve desired miscibility, as well as a desired release rate for the incorporated bioactive material. Highly preferred thermoplastic polymers are those having solubility parameters such as a low degree of crystallization, a low degree of hydrogen bonding, low solubility in water, and high solubility in organic solvents.

According to the practice of the invention, the liquid composition of thermoplastic polymer, solvent, rate modifying agent and bioactive material is a stable liquid substance. Depending on the bioactive material and solvent chosen, either a homogenous solution of the bioactive material in organic solvent, or a suspension or dispersion of the bioactive material in the solvent results. In either case, the thermoplastic polymer is substantially soluble in the organic solvent. Upon placement of the liquid composition into the aqueous medium inside or outside the body, the solvent will dissipate and the polymer will solidify to form the polymer system having the bioactive material within a solid polymeric matrix.

Organic Solvents

The solvents used in the thermoplastic compositions of the present invention are preferably pharmaceutically acceptable, water-miscible, and biocompatible. Preferably, they cause relatively little, if any, tissue irritation or necrosis at the site of the injection and implantation. The solvent is water-miscible so that it will quickly disperse from the polymeric composition into the aqueous medium such as body fluids. Concomitant with the dispersion of solvent the thermoplastic polymer coagulates into the solid polymer system. As the thermoplastic polymer coagulates, the solvent dispersion causes pore formation within the polymer system. As a result, the liquid composition containing thermoplastic polymer, solvent, rate modifying agent and bioactive substance alone will form a porous solid polymer system.

Suitable solvents include those liquid organic compounds meeting the foregoing criteria. Examples include, but are not limited to, N-methyl-2-pyrrolidone (NMP); 2-pyrrolidone (2-pyrol); $C_2$–$C_6$ alkanols; 2-ethoxyethanol; alkyl esters such as 2-ethoxyethyl acetate, methyl acetate, ethyl acetate, propylene carbonate, ethyl lactate; ethylene glycol dimethyl ether; propylene glycol; alkyl ketones such as acetone, methyl ethyl ketone; dimethylformamide; dimethyl sulfoxide; dimethyl sulfone; tetrahydrofuran; cyclic alkyl amides such as caprolactam; decylmethyl sulfoxide; oleic acid; N,N-dimethyl-m-toluamide; and 1-dodecylazacycloheptan-2-one. The preferred solvents are N-methyl-2-pyrrolidone, 2-pyrrolidone, dimethyl sulfoxide, propylene carbonate and ethyl lactate due, at least in part, to their solvating ability and their biocompatibility.

The solvents for the thermoplastic polymer liquid compositions of the present invention are chosen for compatibility and appropriate solubility of the polymer and solvent. Lower molecular weight thermoplastic polymers will normally dissolve more readily in the solvents than high molecular weight polymers. As a result, the concentration of a thermoplastic polymer dissolved in the various solvents differs depending upon type of polymer and its molecular weight. Conversely, the higher molecular weight thermoplastic polymers will tend to coagulate or solidify faster than the very low molecular weight thermoplastic polymers. Moreover, the higher molecular weight polymers tend to give higher solution viscosities than the low molecular weight materials. Thus, for advantageous injection efficiency, in addition to advantageous release rate, the molecular weight and the concentration of the polymer in the solvent are controlled.

A solvent mixture can be used to increase the coagulation rate of thermoplastic polymers that exhibit a slow coagulation or setting rate. In such a system one component of the mixture is typically a good solvent for the thermoplastic polymer, and the other component is a poorer solvent or a nonsolvent. The two liquids are mixed at a ratio such that the thermoplastic polymer is still soluble, but precipitates with the slightest increase in the amount of nonsolvent, such as water in a physiological environment. By necessity, the solvent system must be miscible with both the thermoplastic polymer and water. An example of such binary solvent system is the use of NMP and ethanol for low molecular weight DL-PLA. The addition of ethanol to the NMP/polymer solution increases its coagulation rate significantly.

Polymer Molecular Weight

It has been discovered that the molecular weight of the polymer used in the present invention distinctly affects the rate of bioactive material release as long as the liquid composition has been used as an intermediate. Under these conditions, as the molecular weight of the polymer increases, the rate of bioactive material release from the system decreases, passes through a minimum, and then increases again. This phenomenon can be advantageously used in the formulation of systems for the controlled release of various bioactive materials. For relatively quick release of a bioactive material, polymer molecular weight on either side of the minimum for that particular polymer can be chosen to provide the desired release rate. For release of a bioactive material over a relatively long period of time, a polymer molecular weight in the vicinity of the minimum for the particular polymer can be chosen.

Prior to the present invention, it was known that for most, if not all, polymers, the higher the molecular weight of a polymeric composition, the slower the rate of bioactive material release. This was believed to be a result of chain entanglements in the higher molecular weight polymer, which were believed to slow down the diffusion of drug molecules through the polymer matrix. In contrast, it has been surprisingly discovered that for polymer matrices formed through intermediacy of the liquid composition of the invention, the release rate of a bioactive substance follows a "U" shaped curve as the molecular weight of the polymer increases. Accordingly, a polymer system can be produced with an optimum polymer molecular weight range for the release of bioactive substances over a selected length of time.

For the polymer system of the present invention, the typical minimum rate of release of the incorporated bioactive material occurs at an inherent viscosity (I.V. in deciliters/gm) of about 0.2 but can vary depending on the particular components of the composition. For most systems it is preferred to adjust the molecular weight of the polymer to at least about 0.2 I.V. (15,000 molecular weight as determined by gel permeation chromatography in comparison to polystyrene) for a more sustained release of the bioactive material. Typically, acceptable sustained release rates are obtained if the molecular weight is below about 0.8 I.V. (100,000 molecular weight). More preferably, the molecular weight is adjusted to be within a range of about 0.2–0.5 I.V., for effective sustained release. For a poly(DL-lactide) or a lactide-co-glycolide system, as discussed below, the desired molecular weight range is about 0.2–0.5 I.V. If a molecular weight of a specific polymer is chosen from these parameters and the release of the bioactive substance is too slow or too fast, the rate can be varied simply by determining a few experimental points along the U curve for that polymer and adjusting the molecular weight accordingly.

The molecular weight of a polymer can be varied by any of a variety of methods. The choice of method is typically determined by the type of polymer composition. For example, if a thermoplastic polymer is used that is biodegradable by hydrolysis, the molecular weight can be varied by controlled hydrolysis, such as in a steam autoclave. Typically, the degree of polymerization can be controlled, for example, by varying the number and type of reactive groups and the reaction times.

Rate Modifying Agents

It has been discovered that under the conditions of the invention, rate modifying agents provide significantly improved control to the sustained release character of the polymer system of the present invention. The combination of a rate modifying agent and matrix polymer as influenced by the interaction of the liquid composition with an aqueous medium according to the present invention has the surprising effect of retarding the release of the bioactive material. This effect contrasts with the knowledge and belief in the art. Under typical, known circumstances, which do not result from the interaction of the liquid composition and an aqueous medium, use of a rate modifying agent within a sustained release matrix will only increase the rate of release of the pharmaceutical compound within the matrix. Thus, under most known circumstances, it is difficult, if not impossible, to slow down or retard the release of a medicament from an implant.

As practiced according to the present invention, the use of a rate modifying agent in the polymer system of the present invention can be adapted to cause a decrease in the range of multiple orders of magnitude (e.g., 1 to 10 to 100), preferably up to a ten-fold decrease, in the release rate of the bioactive material relative to that of the same polymer matrix without the rate modifying agent. For example, naltrexone and doxycycline are substantially completely released from a polymer matrix of poly(DL-lactide) within about two to three days in vitro. With the addition of a rate modifying agent (e.g., ethyl heptanoate) and formation of the polymer system through interaction of the liquid composition and an aqueous medium, the release rate can be slowed to produce substantially complete release of the drug within about seven days. With the use of a greater amount of rate modifying agent according to the invention, the period of time can be increased to about fourteen days. By appropriate choice of the polymer molecular weight in optional combination (i.e., from none to significant proportions) with the rate modifying agent, the rate and extent of bioactive material release from the polymer system can be varied from very fast to very slow.

Rate modifying agents useful in the invention are typically miscible with the polymer. That is, the rate modifying agent and polymer are chosen for a particular composition such that the intermolecular forces of each are similar. Rate modifying agents can be either water-soluble or water-insoluble. Preferably, they are water-insoluble, i.e., immiscible. The specific rate modifying agent chosen for a polymer system is preferably more hydrophobic than the organic solvent of choice for that polymer system. It is also preferably a high boiling liquid.

Although it is not intended to be a limitation of the invention, it is believed the rate modifying agent affects the release rate of the polymer system of the present invention by causing the formation of a heretofore unknown distinctive macromolecular structure within the skin and core of the implant as the implant is formed. The distinctive structure is believed to slow down the cross-diffusion of bioactive material and body fluid. It is believed to be absent from implants formed without rate modifying agent or those containing rate modifying agent but which are not prepared through the intermediacy of the liquid composition. Irrespective of the mechanism of action, the effect controls the release characteristics of the polymer system of the invention.

The rate modifying agent chosen typically imparts to an implant a glass transition temperature (Tg) of less than about 55° C., preferably less than about 50° C., and more preferably less than about 37° C. such that the implant is soft, resilient, and flexible in the body.

The rate modifying agents used in the present invention are pharmaceutically acceptable. Typically, the rate modifiers are organic compounds that substitute as the complementary molecules for secondary valence bonding that typically occurs between polymer molecules. Such compounds increase the flexibility and ability of the polymer molecules to slide past each other. The chemical formulas of such compounds will exhibit hydrophobic and hydrophilic regions so as to effect secondary valence bonding. Such organic compounds are often characterized as "plasticizers". However, typical "plasticizers" are not the only compounds that function as rate modifying agents in the polymer system of the present invention to control the rate of release of a bioactive material. Other useful rate modifying agents include fatty acids, triglycerides, other hydrophobic compounds and some organic solvents.

Specific examples of rate modifying agents include, but are not limited to esters of mono-, di-, and tricarboxylic acids, such as 2-ethoxyethyl acetate, methyl acetate, ethyl acetate, diethyl phthalate, dimethyl phthalate, dibutyl phthalate, dimethyl adipate, dimethyl succinate, dimethyl oxalate, dimethyl citrate, triethyl citrate, acetyl tributyl citrate, acetyl triethyl citrate, glycerol triacetate, di(n-butyl) sebecate, and the like; polyhydroxy alcohols, such as propylene glycol, polyethylene glycol, glycerin, sorbitol, and the like; fatty acids; triesters of glycerol, such as triglycerides, epoxidized soybean oil, and other epoxidized vegetable oils; sterols, such as cholesterol; alcohols, such as $C_6$–$C_{12}$ alkanols, 2-ethoxyethanol, and the like. Mixtures of rate modifying agents, such as glycerin/propylene glycol, sorbitol/glycerine, ethylene oxide/propylene oxide, and butylene glycol/adipic acid, can also be used in the polymer systems of the invention.

The choice of rate modifying agent employed depends on the mixture of polymers and the solvent in the thermoplastic system. Preferred rate modifying agents include dimethyl citrate, triethyl citrate, ethyl heptanoate, glycerin, and hexanediol.

The quantity of rate modifying agent in the system will vary depending on the release rate of the medicament desired. Typically, the rate modifying agent is present in an amount up to about 15%, preferably up to about 10%, based upon the total weight of the system.

Polymer Concentration

The concentration of the polymer in the system can also be varied to adjust the release rate of the incorporated bioactive material. It has been discovered that the more dilute the polymer concentration, the more readily the bioactive material will be released. For example, in a system containing 5 percent flurbiprofen and a polymer concentration of 55 percent poly(DL-lactide), a cumulative release of approximately 11.4 percent at day 1 and 23 percent at day 7 is seen. With a polymer concentration of 45 percent, the cumulative percent release at day 1 is 23 percent and about 40 percent at day 7.

This effect can be used in combination with other methods to more effectively control the release of the incorporated medicament as desired. For example, by adjusting the concentration of the polymer, and bioactive material if desired, along with the control of the molecular weight and the amount of rate modifying agent, a wide range of release rates can be obtained.

Pore-Forming Agents

Other additives can be used to advantage in further controlling the desired release rate of a bioactive material for a particular treatment protocol. For example, if the thermoplastic polymer liquid composition is too impervious to water, a pore-forming agent can be added to generate additional pores in the matrix. Any biocompatible water-soluble material can be used as the pore-forming agent. These agents can be either soluble in the liquid composition or simply dispersed within it. They are capable of dissolving, diffusing or dispersing out of both the coagulating polymer matrix and the formed polymer system whereupon pores and microporous channels are generated in the matrix and system. The amount of pore-forming agent (and size of dispersed particles of such pore-forming agent, if appropriate) within the composition will directly affect the size and number of the pores in the polymer system.

Other factors can also influence the size and/or diameter of the pores formed in the polymer system. For example, the amount of organic solvent, and the rate at which the polymer system solidifies, can all affect the porosity of the polymer system. Although a generally microporous matrix without a resolved core and skin can be produced according to the invention, typically, without an additional pore-forming agent a polymer system formed from the liquid composition is composed of a surface skin and inner core. The surface skin is typically less porous, and even relatively nonporous, when compared to the inner core. The inner core can contain pores with a diameter of about 10–1000 um. With additional pore-forming agent, the pore sizes of the core and skin become substantially uniform such that they both have pores in the range of 10 to 1000 um.

The concentration of pore-forming agent relative to thermoplastic polymer in the composition will vary according to the degree of pore-formation desired. Generally, this concentration will range from about 0.01 to 1 gram of pore-forming agent per gram of polymer. If the agent is soluble in the liquid composition, then the mixing or distribution of the agent in the liquid composition and the aggregation when the thermoplastic coagulates will determine the size of the resultant pores as the agent dissolves out of the polymer matrix.

Pore-forming agents include, any pharmaceutically acceptable organic or inorganic substance that is substantially miscible in water and body fluids and will dissipate from the forming and formed matrix into aqueous medium or body fluids or water-immiscible substances that rapidly degrade to water-soluble substances. The pore-forming agent may be soluble or insoluble in the polymer liquid composition of the invention. In the liquid composition of the invention, it is further preferred that the pore-forming agent is miscible or dispersible in the organic solvent to form a uniform mixture. Suitable pore-forming agents include, for example, sugars such as sucrose and dextrose, salts such as sodium chloride and sodium carbonate, and polymers such as hydroxylpropylcellulose, carboxymethylcellulose, polyethylene glycol, and polyvinylpyrrolidone. The size and extent of the pores can be varied over a wide range by changing the molecular weight and percentage of pore-forming agent incorporated into the polymer system.

Bioactive Materials

The terms "drug," "medicament," or "bioactive material" (i.e., biologically active material) as used herein include, biologically, physiologically, or pharmacologically active substances that act locally or systemically in the human or animal body. Various forms of the medicaments or biologically active materials can be used which are capable of being released from the polymer matrix into adjacent tissues or fluids. The medicaments are at least very slightly water-soluble, preferably moderately water-soluble, and are diffusible through the polymeric composition. They can be acidic, basic, or salts. They can be neutral molecules, polar molecules, or molecular complexes capable of hydrogen bonding. They can be in the form of ethers, esters, amides and the like, which are biologically activated when injected into the human or animal body.

Generally, any drugs or bioactive materials that can be dissolved or dispersed in an aqueous environment can be utilized in the liquid composition and polymer system of the present invention. For example, the bioactive material can be a penicillin or cephalosporin antibiotic, a hormone such as ACTH, estrogen or testosterone, a protein such as a monoclonal antibody or an essential human or animal enzyme, insulin or an insulin precursor, a vaccine or serum substance useful in the treatment of viral diseases, an activator or inhibitor of a specific enzyme, a releasing factor for a physiologically active substance, or any other suitable substance.

Representative drugs or bioactive materials that can be used in the injectable sustained release compositions of the present invention include, but are not limited to, peptide drugs, protein drugs, such as enzymes, insulin, interleukin, platelet anticoagulating agent, hormones, calcitonin, vasopressin, desensitizing agents, bronchodilating agents, anti-infective agents, antibiotics, antimicrobial agents, anti-allergenics, androgenic steroids, decongestants, hypnotics, steroidal and nonsteroidal anti-inflammatory agents, anticholinergics, sympathomimetics, sedatives, miotics, steroids, corticosteroids, regulatory agents, nephritic agents, psychic energizers, tranquilizers, vaccines, estrogens, progestational agents, humoral agents, prostaglandins, analgesics, antispasmodics, antimalarials, antihistamines, cardioactive agents, male and female birth control agents, tissue growth factors, antiparkinsonian agents, antihypertensive agents, α-adrenergic blocking agents, nutritional agents, and alkaloid pharmaceutical agents.

The bioactive material may also be a substance, or metabolic precursor thereof, which is capable of promoting growth and survival of cells and tissues, or augmenting the activity of functioning cells, as for example, blood cells, neurons, muscle, bone marrow, bone cells and tissues, and the like. For example, the bioactive material may be a nerve growth promoting substance, as for example, a ganglioside, phosphatidylserine, a nerve growth factor, brain-derived neurotrophic factor, a fibroblast growth factor, and the like. In particular, the in situ implants are capable of enhancing regeneration of the periodontium by providing an outer surface having a porosity which serves as a physical barrier between an exposed root surface and encroaching epithelial cells to promote guided tissue regeneration.

To promote tissue growth, the biologically active material may be a tissue growth factor substance. Suitable tissue growth promoting agents include, for example, fibronectin (FN), endothelial cell growth factor (ECGF), cementum attachment extracts (CAE), human growth hormone (HGH), a periodontal ligament cell growth factor, animal growth hormones, fibroblast growth factor (FGF), platelet derived growth factor (PDGF), epidermal growth factor (EGF), protein growth factor, interleukin-1 (IL-1), transforming growth factor (TGF-α or TGF-β), insulin-like growth factor II (IGF-II), human alpha thrombin (HAT), osteoinductive factor (OIF), bone morphogenetic protein (BMP) or protein derived therefrom, demineralized bone matrix, and releasing factors thereof. Further, the agent may be a bone growth promoting substance such as hydroxyapatite, tricalcium phosphate, a di- or polyphosphonic acid, an anti-estrogen, a sodium fluoride preparation, a substance having a phosphate to calcium ratio similar to natural bone, and the like. A bone growth promoting substance may be in the form, as for example, of bone chips, bone crystals or mineral fractions of bone and/or teeth, a synthetic hydroxyapatite, or other suitable form. The agent may further be capable of treating metabolic bone disorders such as abnormal calcium and phosphate metabolism, by for example, inhibiting bone resorption, promoting bone mineralization, or inhibiting calcification.

The bioactive material can be miscible in the polymer and/or solvent to provide a homogenous mixture with the polymer, or insoluble in the polymer and/or solvent to form a suspension or dispersion with the polymer.

Upon formation of the polymer system from the liquid composition, the biologically active material becomes incorporated into the polymer matrix. After implantation of the externally formed polymer system or insertion of the liquid composition to form in situ the polymer system, the bioactive material will be released from the matrix into the adjacent tissues or fluids by diffusion and polymer degradation mechanisms. Manipulation of these mechanisms also can influence the release of the bioactive material into the surroundings at a controlled rate. For example, the polymer matrix can be formulated to degrade after an effective an/or substantial amount of the bioactive material is released from the matrix. Release of a material having a low solubility in water, as for example a peptide or protein, typically requires the degradation of a substantial part of the polymer matrix to expose the material directly to the surrounding tissue fluids. Thus, the release of the biologically active material from the matrix can be varied by, for example, the solubility of the bioactive material in water, the distribution of the bioactive material within the matrix, or the size, shape, porosity, solubility and biodegradability of the polymer matrix, among other factors. The release of the biologically active material from the matrix is controlled relative to its intrinsic rate by varying the polymer molecular weight and by adding a rate modifying agent to provide a desired duration and rate of release, as described above.

The polymer system is formulated to contain the bioactive material in an amount effective to provide a desired biological, physiological and/or therapeutic effect. The "effective amount" of a biologically active material incorporated into the injectable polymeric composition of the invention depends on a variety of factors, such as the desired release profile, the concentration of bioactive material required for a desired biological effect, and the period of time over which the bioactive material needs to be released for desired treatment. Ultimately, this amount is determined by the human or animal patient's physician or veterinarian, respectively, who will apply his experience and wisdom in prescribing the appropriate kind and amount of bioactive material to provide therapy for the patient. There is generally no critical upper limit on the amount of bioactive material incorporated into the polymer solution. The only limitation is a physical limitation for advantageous application, i.e., the bioactive material should not be present in such a high concentration that the solution or dispersion viscosity is too high for injection. The lower limit of bioactive material incorporated into the polymer system typically depends only on the activity of the bioactive material and the period of time desired for treatment.

Administration of the liquid composition or the externally formed polymer system of the invention ultimately will be accomplished according to the wisdom and protocol of the patient's attending health care professional such as a physician, or if appropriate, a dentist or DVM. Choice of the particular composition will depend upon the condition to be treated, which choice will be made by the attending health care professional. When the liquid composition is injected into soft tissue to provide a sustained release implant, the resulting polymer system will both release the bioactive material and biodegrade as designed so that no residue remains. When the liquid composition is injected into a soft tissue defect and a suitable bioactive material for assisting in collagen formation is in the composition, the resulting polymer system fills the defect and provides a support structure upon which natural collagen tissue can grow. This collagen tissue gradually replaces the biodegradable polymer. With hard tissue such as bone, the biodegradable polymer containing a bone growth factor supports the growth of new bone cells. These new bone cells eventually replace the degrading polymer.

The following examples are set forth as representative specific and preferred embodiments of the present invention. These examples are not to be construed as limiting the scope of the invention in any manner. It should be understood that many variations and modifications can be made while remaining within the spirit and scope of the invention.

EXAMPLE 1

Effect of Rate Modifying Agent

Formulations were prepared with poly(DL-lactide), N-methylpyrrolidone, and naltrexone hydrochloride (3.0%). The formulations differed in the amount of ethyl heptanoate (rate modifying agent). Release was into pH 7.2 phosphate buffered saline (PBS). The polymer formulation was precipitated into the PBS by expelling it from a 1 mL syringe. The PBS solutions were placed in a 37° C. shaker bath. At regular intervals the PBS solution was removed, and replaced with fresh PBS. The PBS solutions were analyzed by UV absorption at 285 nm to determine naltrexone hydrochloride concentration. The cumulative percent released is tabulated in Table 1.

TABLE 1

EFFECT OF RATE MODIFYING AGENT CONTENT ON RELEASE OF NALTREXONE HYDROCHLORIDE

| Day | 0% | 5% | 10% |
|-----|------|------|------|
| 1 | 71.3 | 27.6 | 5.7 |
| 2 | 85.2 | 32.9 | 10.0 |
| 4 | 96.4 | 41.2 | 15.5 |
| 7 | 97.4 | 44.6 | 15.5 |
| 10 | 100.8 | 49.2 | 17.7 |
| 17 | 101.8 | — | — |
| 20 | — | 64.7 | 33.6 |

EXAMPLE 2

Effect of Rate Modifying Agent with Doxycycline Hyclate

Formulations were prepared with poly(DL-lactide), N-methyl-2-pyrrolidone, and 5% doxycycline hyclate. One formulation contained 5% ethyl heptanoate as a rate modifying agent and the other formulation served as a control with no ethyl heptanoate being present. Release of doxycycline from the formulations and analysis of the release rates were performed as described in Example 1 except a pH 6.85 phosphate buffered saline was used. The cumulative percent released is tabulated in Table 2.

TABLE 2

EFFECT OF RATE MODIFYING AGENT CONTENT ON RELEASE OF DOXYCYCLINE HYCLATE

| Day | 0% | 5% |
|-----|------|-----|
| 1   | 23.2 | 1.6 |
| 8   | 64.0 | 3.0 |
| 23  | 71.9 | 6.3 |

EXAMPLE 3

Effect of Molecular Weight with Poly(DL-lactide-co-glycolide)

Formulations were prepared using various molecular weights of 50:50 poly(DL-lactide-co-glycolide) (PLG). The molecular weights of the polymers were estimated by an inherent viscosity (I.V.) measurement in chloroform, with lower I.V. values corresponding to lower molecular weights. The formulations were prepared by dissolving the polymer in N-methyl-2-pyrrolidone (NMP) to give a 50% solution. To this solution was added naltrexone free base to give a formulation with the overall composition of 5% naltrexone free base, 47.5% PLG and 47.5% NMP.

A controlled size drop of formulation was expelled from a 1 mL syringe into pH 7.4 phosphate buffered saline (PBS). The PBS was maintained at 37° C. with agitation. At regular intervals the PBS was removed and replaced with fresh PBS. The release solutions removed were analyzed for naltrexone content by high performance liquid chromatography (HPLC). Cumulative percent release data are presented in Table 3.

TABLE 3

EFFECT OF MOLECULAR WEIGHT ON RELEASE OF NALTREXONE FREE BASE FROM 50:50 POLY (DL-LACTIDE-CO-GLYCOLIDE)

| | (Polymer I.V.) | | | | |
|---|---|---|---|---|---|
| Day | 0.19 | 0.35 | 0.52 | 0.61 | 0.73 |
| 1  | 10.2 | 7.6  | 9.2  | 27.5 | 46.7 |
| 2  | 25.0 | 10.9 | 11.2 | 33.3 | 55.5 |
| 4  | 36.3 | 16.2 | 14.9 | 39.9 | 68.0 |
| 7  | 43.5 | 26.5 | 21.5 | 45.0 | 73.6 |
| 10 | 54.7 | 34.6 | 31.9 | 56.4 | 77.8 |

EXAMPLE 4

Effect of Molecular Weight with Poly(DL-lactide)

Formulations were prepared with 10% naloxone hydrochloride, 45% poly(DL-lactide) (PLA) and 45% NMP. In this trial, three molecular weights of PLA were used. The lower and higher I.V. polymers were obtained from commercial sources whereas the intermediate molecular weight polymer (I.V.=0.21) was prepared by autoclaving a higher molecular weight PLA. Release of naloxone from the formulations and analysis of the release rates were performed as described in Example 1, except for the naloxone content being determined by ultraviolet spectroscopy (UV) instead of HPLC. Cumulative percent release data are presented in Table 4.

TABLE 4

EFFECT OF MOLECULAR WEIGHT ON RELEASE OF NALOXONE HYDROCHLORIDE FROM POLY (DL-LACTIDE)

| | (Polymer I.V.) | | |
|---|---|---|---|
| Hours | 0.11 | 0.21 | 0.33 |
| 3  | 72.6  | 17.2 | 29.6 |
| 6  | 76.9  | 29.7 | 40.0 |
| 12 | 80.4  | 43.7 | 52.6 |
| 24 | 86.9  | 54.4 | 69.7 |
| 48 | 98.6  | 59.3 | 82.4 |
| 96 | 101.3 | 62.7 | 90.5 |

EXAMPLE 5

Polymer Autoclaving

Because poly(DL-lactide) is degradable by hydrolysis, lower molecular weight samples can be prepared by reacting a higher molecular weight polymer sample with water. This is most conveniently done in a controlled manner in a steam autoclave.

The polymer, in powdered form, is spread thinly in a teflon-lined glass petri dish. The polymer is placed in a steam autoclave at 22 psi. The time the polymer is allowed to remain in the autoclave determines the final molecular weight (longer times=lower molecular weight). The decision on the amount of time is semi-empirical at best. The polymer is removed from the autoclave, cooled and dried in vacuo. The dried polymer can be purified by dissolving it in methylene chloride, and precipitating the resulting solution in methanol.

After complete drying in vacuo, the polymer molecular weight can be determined by gel permeation chromatography (GPC), or estimated by inherent viscosity. The monomer ratio can be determined by nuclear magnetic resonance (NMR).

What is claimed is:

1. A composition suitable for in situ formation of an implant in an animal, comprising:
   (a) a pharmaceutically acceptable, biodegradable thermoplastic polymer that is insoluble in aqueous or body fluids;
   (b) a biocompatible organic solvent which solubilizes the thermoplastic polymer, is miscible to dispersible in aqueous or body fluids, and is capable of dissipating from the polymer system into surrounding tissue fluid whereupon the thermoplastic polymer forms the implant; and
   (c) a biologically active agent capable of enhancing bone growth.

2. The composition of claim 1, further comprising a release rate modifying agent.

3. The composition of claim 1 wherein the biologically active material is demineralized bone matrix.

4. The composition of claim 1 wherein the biological active material is bone morphogenic protein.

* * * * *